(12) United States Patent
Usami et al.

(10) Patent No.: US 8,920,992 B2
(45) Date of Patent: Dec. 30, 2014

(54) HYDROGEN CONCENTRATION MEASUREMENT DEVICE AND FUEL CELL SYSTEM

(75) Inventors: Sho Usami, Susono (JP); Yasushi Araki, Gotemba (JP)

(73) Assignee: Toyota Jidosha Kabushiki Kaisha, Toyota-shi (JP)

(*) Notice: Subject to any disclaimer, the term of this patent is extended or adjusted under 35 U.S.C. 154(b) by 765 days.

(21) Appl. No.: 13/122,064

(22) PCT Filed: Jun. 8, 2009

(86) PCT No.: PCT/JP2009/060465
§ 371 (c)(1),
(2), (4) Date: Mar. 31, 2011

(87) PCT Pub. No.: WO2010/143254
PCT Pub. Date: Dec. 16, 2010

(65) Prior Publication Data
US 2011/0177403 A1 Jul. 21, 2011

(51) Int. Cl.
*H01M 8/04* (2006.01)
*G01N 27/407* (2006.01)
*H01M 8/10* (2006.01)

(52) U.S. Cl.
CPC ...... *H01M 8/04462* (2013.01); *H01M 8/04895* (2013.01); *H01M 2250/00* (2013.01); *H01M 2008/1095* (2013.01); *H01M 8/04902* (2013.01); *H01M 8/0444* (2013.01); *H01M 8/04544* (2013.01); *Y02E 60/50* (2013.01); *G01N 27/4074* (2013.01); *H01M 8/04097* (2013.01); *H01M 8/04552* (2013.01)
USPC .......................................... 429/428; 429/430

(58) Field of Classification Search
USPC ....................................................... 429/415
See application file for complete search history.

(56) References Cited

U.S. PATENT DOCUMENTS

| | | | |
|---|---|---|---|
| 6,652,723 | B1 | 11/2003 | Nadanami et al. |
| 6,977,121 | B2 | 12/2005 | Balliet et al. |
| 2003/0089604 | A1 | 5/2003 | Nadanami et al. |
| 2004/0026265 | A1 | 2/2004 | Nadanami et al. |
| 2004/0197621 | A1* | 10/2004 | Balliet et al. ............. 429/22 |
| 2005/0118468 | A1 | 6/2005 | Adams et al. |
| 2009/0226777 | A1 | 9/2009 | Kanno |

FOREIGN PATENT DOCUMENTS

| | | |
|---|---|---|
| JP | 04 034356 | 2/1992 |
| JP | 2001 215214 | 8/2001 |
| JP | 2002 303602 | 10/2002 |
| JP | 2003 207483 | 7/2003 |
| JP | 2003 270200 | 9/2003 |
| JP | 2004 212157 | 7/2004 |
| JP | 2005 127969 | 5/2005 |
| JP | 2006 019120 | 1/2006 |
| JP | 2006 522451 | 9/2006 |
| JP | 2007 220509 | 8/2007 |
| JP | 2008 047329 | 2/2008 |

OTHER PUBLICATIONS

International Search Report issued Mar. 23, 2010 in PCT/JP09/060465 filed Jun. 8, 2009.

* cited by examiner

*Primary Examiner* — Ula C. Ruddock
*Assistant Examiner* — Jacob Marks
(74) *Attorney, Agent, or Firm* — Oblon, Spivak, McClelland, Maier & Neustadt, L.L.P.

(57) ABSTRACT

In a hydrogen concentration measurement device that employs a proton conducting electrolyte membrane, more stable measurement of hydrogen concentration that is less susceptible to temperature and humidity state of measurement target gas becomes possible.

A hydrogen concentration measurement device for measuring concentration of hydrogen contained in measurement target gas, including a hydrogen permeation module having an entrance electrode and an exit electrode provided with a proton conducting electrolyte membrane sandwiched therebetween, the hydrogen permeation module selectively permeating hydrogen contained in the measurement target gas to the exit electrode by having the measurement target gas introduced into the entrance electrode and also by having current flowing between the entrance electrode and the exit electrode, and concentration of hydrogen contained in the measurement target gas is calculated based on, with the target gas introduced into the entrance electrode and with the current flowing between the entrance electrode and the exit electrode, a reaching time period ranging from a predetermined start time at which the current was initially applied to a time at which time rate of change of applied voltage between the entrance electrode and the exit electrode reaches a predetermined time rate of change.

5 Claims, 6 Drawing Sheets

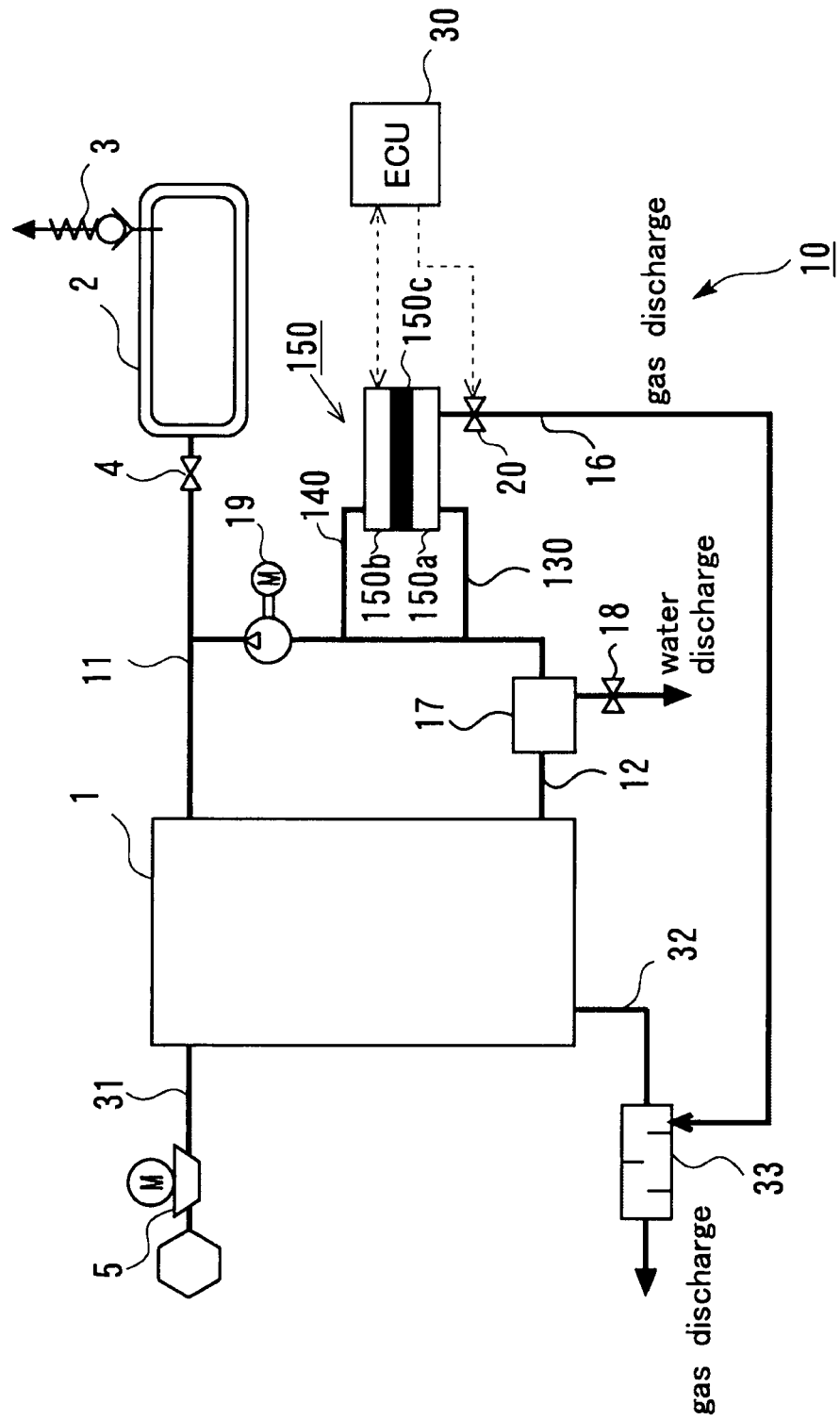

HYDROGEN CONCENTRATION MEASUREMENT DEVICE AND FUEL CELL SYSTEM

TECHNICAL FIELD OF THE INVENTION

The present invention relates to a hydrogen concentration measurement device for measuring concentration of hydrogen contained in gas to be targeted for measurement.

BACKGROUND ARTS

For a fuel cell system that generates electrical power through electrochemical reaction between hydrogen-containing fuel gas and oxidizing gas, a technique is widely known that promotes reuse of hydrogen contained in anode offgas by circulating the anode offgas to anode electrode side of a fuel cell, in order to use the hydrogen contained in the anode offgas efficiently for the generation of electrical power. In such hydrogen circulation type of fuel cell system, it is known that nitrogen permeated from cathode electrode side through an electrolyte membrane of the fuel cell, impurities contained in the fuel gas, and the like accumulate on the anode electrode side of the fuel cell and reduce hydrogen partial pressure, thus resulting in decrease in power generating efficiency of the fuel cell.

So, a technique was made public that provides an electrochemical cell that condenses impurities by selectively permeating hydrogen contained in anode offgas in a circulation pathway for circulating anode offgas as described above for the purpose of maintaining power generating efficiency, and discharges the impurities in the anode offgas that were condensed as a result of the hydrogen permeation out of the system (see Patent Document 1, for example). In case of discharging anode offgas out of the system as above, it is important to reduce an amount of hydrogen contained therein as much as possible also from the viewpoint of efficient utilization of hydrogen, and also because of this reason, it is required to measure concentration of hydrogen in the gas more accurately.

As a technique for measuring concentration of hydrogen contained in measurement target gas, the technique described in Patent Document 2 is disclosed here. This technique, in a hydrogen concentration sensor that employs a proton conducting electrolyte membrane, makes an attempt to achieve measurement of hydrogen concentration by keeping diffusion speed of measurement target gas at an entrance electrode lower than proton conducting ability between the entrance electrode and an exit electrode, thereby reducing influence of moisture contained in the measurement target gas.

DOCUMENTS OF PRIOR ART

Patent Documents

Patent Document 1: Japanese Patent Laid-Open Publication No. 2006-19120
Patent Document 2: Japanese Patent Laid-Open Publication No. 2001-215214
Patent Document 3: Japanese Patent Laid-Open Publication No. 2008-47329
Patent Document 4: Japanese Patent Laid-Open Publication No. 2003-207483
Patent Document 5: Japanese Patent Laid-Open Publication No. 2005-127969
Patent Document 6: Japanese Patent Laid-Open Publication No. Heisei 4-34356

SUMMARY OF THE INVENTION

Problem to be Solved by the Invention

In case where a proton conducting electrolyte membrane is employed for measurement of concentration of hydrogen contained in measurement target gas, along with increased proportion of materials other than hydrogen (hereinafter referred to as "impurities") to the measurement target gas at entrance electrode side into which the measurement target gas is introduced, an effectively used surface area of the electrode is decreased, and results in variation of voltage applied between electrodes. Therefore, in conventional techniques, measurement of concentration of hydrogen in measurement target gas is performed based on variation of applied voltage between electrodes itself.

However, on the other hand, a proton conducting electrolyte membrane tends to have its proton transfer resistance varied under the influence of wet state of measurement target gas to be introduced. For example, moisture state within the electrolyte membrane differs significantly between a case where dry, high temperature measurement target gas is introduced into an entrance electrode and a case where wet, low temperature measurement target gas is introduced into the same entrance electrode, so that result of measurement may be different even if the respective measurement target gases have a same hydrogen concentration. That is, if trying to measure hydrogen concentration based on variation of applied voltage itself, it is difficult to discriminate if the voltage variation is due to concentration of impurities in measurement target gas or to moisture state of electrolyte membrane, and thus, accurate measurement of hydrogen concentration may become difficult.

Especially, when using a hydrogen concentration measurement device that employs a proton conducting electrolyte membrane in a system where temperature and wet state of measurement target gas may vary relatively significantly, the afore-mentioned problems are serious and have non-negligible influence on precisions of controls by various devices in the system that employ result of hydrogen concentration measurement made by the measurement device.

The present invention is made in view of the afore-mentioned problems, and is purposed to enable more stable measurement of hydrogen concentration that is less susceptible to temperature and humidity state of measurement target gas in a hydrogen concentration measurement device that employs a proton conducting electrolyte membrane.

Means for Solving the Problems

In the present invention, in order to solve the afore-mentioned problems, in a hydrogen concentration measurement device that employs a proton conducting electrolyte membrane, hydrogen concentration is measured by employing, rather than variation of applied voltage between electrodes provided with the electrolyte membrane sandwiched therebetween, a time period that time rate of change of the applied voltage requires to reach a predetermined time rate of change. The applicant of the present invention has found out that transition of the time rate of change of applied voltage is less susceptible to temperature and humidity state of measurement target gas and thus is a relatively stable parameter.

Therefore, more specifically, the present invention relates to a hydrogen concentration measurement device for measuring concentration of hydrogen contained in measurement target gas, including:

a hydrogen permeation module having an entrance electrode and an exit electrode provided with a proton conducting electrolyte membrane sandwiched therebetween, the hydrogen permeation module selectively permeating hydrogen contained in the measurement target gas to the exit electrode by having the measurement target gas introduced into the entrance electrode, and also by having current flowing between the entrance electrode and the exit electrode;

a current control module controlling current flowing between the entrance electrode and the exit electrode in the hydrogen permeation module; and a hydrogen concentration calculation module calculating concentration of hydrogen contained in the measurement target gas based on, with the target gas introduced into the entrance electrode and with the current flowing between the entrance electrode and the exit electrode by the current control module, a reaching time period ranging from a predetermined start time at which the current was initially applied to a time at which time rate of change of applied voltage between the entrance electrode and the exit electrode reaches a predetermined time rate of change.

In the hydrogen permeation module provided in afore-mentioned hydrogen concentration measurement device, hydrogen contained in measurement target gas introduced into the entrance electrode side permeates through the electrolyte membrane as proton by having current flowing between the entrance electrode and the exit electrode. As a result of this hydrogen permeation, impurities in the measurement target gas are condensed at the entrance electrode side and thus have its concentration increased. Therefore, a proportion of hydrogen to impurities contained in the measurement target gas at the entrance electrode side varies as time passes, so that electrical condition between the electrodes also varies as time passes. Concretely, along with increased proportion of impurities to the measurement target gas, an effective surface area of the electrode is decreased, and results in increased applied voltage between the electrodes.

However, as described above, this applied voltage between the electrodes is susceptible to temperature and humidity of the measurement target gas and makes precision of hydrogen concentration measurement instable. Therefore, the present applicant has focused on using time rate of change of applied voltage as a parameter for measurement of hydrogen concentration. This is because the applicant has found out that time rate of change of applied voltage is less susceptible to temperature and humidity of the measurement target gas while strongly reflecting concentration of impurities contained in the measurement target gas. Especially, the reaching time period ranging from a time at which the current was initially applied between the entrance electrode and the exit electrode and thus hydrogen permeation was started by the hydrogen permeation module to a time at which time rate of change of applied voltage reaches the predetermined time rate of change reflects a proportion of hydrogen to impurities contained in the measurement target gas, so that it may be preferable for the hydrogen concentration measurement device that employs the proton conducting electrolyte membrane.

So, in the hydrogen concentration measurement device according to the present invention, the hydrogen concentration calculation module calculates concentration of impurities in the measurement target gas introduced into the entrance electrode, in other words concentration of hydrogen in the measurement target gas, based on the reaching time period ranging from the predetermined start time at which the current was initially applied to a time at which time rate of change of applied voltage between the electrodes reaches the predetermined time rate of change. Here, the predetermined start time refers to a time at which the current was initially applied between the electrodes for execution of the afore-mentioned hydrogen permeation for measurement of hydrogen concentration with respect to the measurement target gas targeted for measurement of its hydrogen concentration. In addition, the predetermined time rate of change only needs to be a time rate of change that allows for calculation of concentration of hydrogen contained in the measurement target gas, and may be set appropriately in light of specific structure and size of the hydrogen concentration measurement device, condition of hydrogen permeation at the hydrogen permeation module (such as magnitude of the current flowing between the electrodes), and the like.

Here, when the calculation of hydrogen concentration based on the afore-mentioned reaching time period is performed by the hydrogen concentration calculation module, it is preferable that the calculation is performed with constant current flowing between the entrance electrode and the exit electrode. By controlling voltage applied between the electrodes such that constant current flows therebetween, it is possible to eliminate influence of temperature and humidity of measurement target gas on the reaching time period that the time rate of change of applied voltage takes to reach the predetermined time rate of change, so that the reaching time period can adequately reflect concentration of hydrogen contained therein. However, this does not exclude the calculation of hydrogen concentration by the hydrogen concentration calculation module based on a reaching time period that is obtained with non-constant current flowing between the electrodes. For example, in the calculation of hydrogen concentration, if the change of current flowing between the electrodes and the reaching time period have a uniform correlation therebetween, then it is possible to measure hydrogen concentration even if the current is non-constant.

Here, the hydrogen concentration measurement device described hereinabove can be employed in a fuel cell system that performs generation of electrical power by a fuel cell. Since the generation of electrical power is performed through electrochemical reaction between hydrogen and oxygen in the fuel cell, measurement of hydrogen concentration by the hydrogen concentration measurement device is required for various purposes. One example is measurement of hydrogen concentration in a hydrogen circulation type of fuel cell system that supplies anode offgas output from a fuel cell to anode electrode side again. In detail, it is a fuel cell system including the hydrogen concentration measurement device as described above, the fuel cell system having hydrogen-containing fuel gas supplied to anode electrode side of a fuel cell for electrochemical reaction therein, and also having a circulation pathway such that a part or all of anode offgas from the fuel cell can be circulated to the anode electrode side of the fuel cell for the electrochemical reaction again, wherein the hydrogen concentration measurement device is disposed such that it is capable of measuring concentration of hydrogen in anode offgas in the circulation pathway by having the anode offgas flowing through the circulation pathway introduced into the entrance electrode. And, the system is configured such that the anode offgas in the circulation pathway is discharged out of the system based on the hydrogen concentration measured by the hydrogen concentration measurement device.

In the hydrogen circulation type of fuel cell system having the circulation pathway as described above, anode offgas is delivered into the anode electrode side again via the circulation pathway for the purpose of efficient utilization of hydrogen. At this time, nitrogen permeated from cathode electrode side of the fuel cell and impurities other than hydrogen contained in the fuel gas accumulate within anode offgas to be circulated, and may result in decrease in power generating efficiency of the fuel cell and damage of the fuel cell. Therefore, it is necessary to remove impurities in the circulation pathway by discharging the anode offgas flowing through the circulation pathway out of the system at appropriate timings. So, by employing result of hydrogen concentration measurement by the hydrogen concentration measurement device according to the present invention, the anode offgas in the circulation pathway can be discharged at appropriate timings with no influence of temperature and humidity of the anode offgas output from the fuel cell. Since temperature and humidity of the anode offgas are varied depending on operational state of the fuel cell, the hydrogen concentration measurement device according to the present invention that is less susceptible to temperature and humidity of measurement target gas is quite useful.

Here, in the afore-mentioned fuel cell system to which the hydrogen concentration measurement device according to the present invention is applied, hydrogen that was permeated to the exit electrode side by the hydrogen permeation module provided in the hydrogen concentration measurement device may also be supplied to the anode electrode side of the fuel cell again. That is, efficient utilization of hydrogen is promoted by supplying hydrogen that was used by the hydrogen permeation module for measurement of hydrogen concentration to the fuel cell again for generation of electrical power therein.

In addition, in the hydrogen circulation type of fuel cell system, an electrochemical cell is sometimes provided on the circulation pathway for hydrogen circulation for the purpose of efficient utilization of hydrogen. This electrochemical cell employs a proton conducting electrolyte membrane, and has many structural commonalities with the permeation module of the hydrogen concentration measurement device according to the present invention. So, by employing this electrochemical cell also as the hydrogen concentration measurement device for measurement of hydrogen concentration, the fuel cell system can be made simple in structure. More specifically, the fuel cell system is a fuel cell system having hydrogen-containing fuel gas supplied to anode electrode side of a fuel cell for electrochemical reaction therein, and also having a circulation pathway disposed such that a part or all of anode offgas from the fuel cell can be circulated to the anode electrode side of the fuel cell for the electrochemical reaction again, the fuel cell system including: an electrochemical cell having an entrance electrode and an exit electrode provided with a proton conducting electrolyte membrane sandwiched therebetween, connected to the circulation pathway such that a part or all of anode offgas discharged from the fuel cell can be supplied to the entrance electrode, selectively permeating hydrogen contained in the anode offgas to the exit electrode by having current flowing between the entrance electrode and the exit electrode, and connected such that the permeated hydrogen can be supplied to the anode electrode side of the fuel cell; and a current control module controlling current flowing between the entrance electrode and the exit electrode in the electrochemical cell. And, for measurement of hydrogen concentration, the system also includes a hydrogen concentration calculation module that calculates concentration of hydrogen contained in the anode offgas based on, with the anode offgas flowing through the circulation pathway introduced into the entrance electrode and with the current flowing between the entrance electrode and the exit electrode by the current control module in the electrochemical cell, a reaching time period ranging from a predetermined start time at which the current was initially applied to a time at which time rate of change of applied voltage between the entrance electrode and the exit electrode reaches a predetermined time rate of change.

With such configuration, the electrochemical cell usually acts as a device for increasing concentration of hydrogen in anode offgas to be circulated by hydrogen permeation, and at the time of hydrogen concentration measurement, the electrochemical cell acts as a device for measuring concentration of hydrogen in anode offgas by employing the configuration of the entrance electrode, exit electrode, and electrolyte membrane provided in the electrochemical cell. At the time of measuring concentration of hydrogen in anode offgas, the electrochemical cell may have different current control than in the usual hydrogen permeation by the current control module, and may also have the same current control as in the usual hydrogen permeation if measurement of hydrogen concentration is possible with the same current control as the usual current control. Irrespective of which current control is performed, hydrogen that was permeated for use in concentration measurement may be employed again by the fuel cell.

In addition, the afore-mentioned fuel cell system may further include: a discharge module disposed on the entrance electrode side of the electrochemical cell, the discharge module discharging at least anode offgas within the entrance electrode out of the system; and a discharge control module controlling discharge of anode offgas by the discharge module based on the hydrogen concentration calculated by the hydrogen concentration calculation module.

On the other hand, as a result of hydrogen permeation by the electrochemical cell, impurities such as nitrogen, contained in anode offgas will be condensed on the entrance electrode side. And, since increased concentration of impurities at the entrance electrode leads to deficiency in hydrogen, and causes various troubles with the electrochemical cell such as deterioration of the electrolyte membrane, it is necessary to discharge anode offgas containing condensed impurities out of the system by the afore-mentioned discharge module. Here, timings to discharge anode offgas by the discharge module are controlled according to hydrogen concentration measured by the electrochemical cell also acting as a hydrogen concentration measurement device, so that discharge of anode offgas can be attained at stably-appropriate timings with no influence of operational condition of the fuel cell.

Effect of the Invention

In a hydrogen concentration measurement device that employs a proton conducting electrolyte membrane, more stable measurement of hydrogen concentration that is less susceptible to temperature and humidity state of measurement target gas becomes possible.

BRIEF DESCRIPTION OF THE DRAWINGS

FIG. 8 is a second diagram showing general configuration of a fuel cell system including the hydrogen concentration sensor shown in FIG. 1.

MODES FOR EMBODYING THE INVENTION

Figure 1:
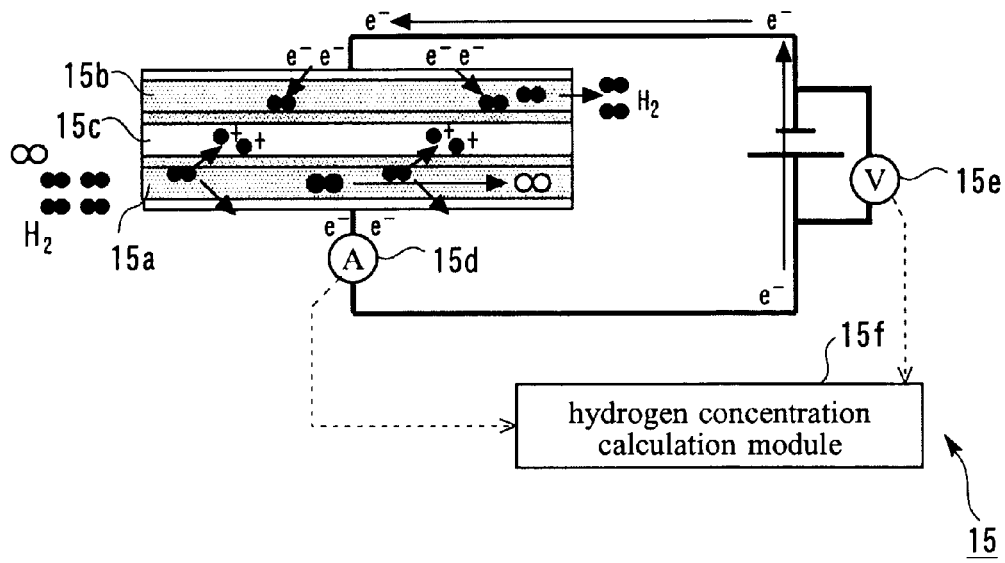
FIG. 1 is a diagram showing general configuration of a hydrogen concentration sensor employing a proton conducting electrolyte membrane, which is a hydrogen concentration measurement device according to an embodiment of the present invention.

Modes for embodying a hydrogen concentration sensor 15 that is a hydrogen concentration measurement device according to the present invention for measuring concentration of hydrogen contained in measurement target gas, and modes for embodying a fuel cell system that is an example of a system to which the hydrogen concentration sensor 15 is applied are now described based on the drawings. FIG. 1 is a diagram showing general configuration of the hydrogen concentration sensor 15. The hydrogen concentration sensor 15 has an entrance electrode 15a and an exist electrode 15b provided with an electrolyte membrane 15c sandwiched therebetween, and is constructed such that gas targeted for measurement of hydrogen concentration is introduced into the entrance electrode 15a.

And, the hydrogen concentration sensor 15 has a hydrogen permeation module that exerts "hydrogen permeation" effect which, by having current flowing between the two electrodes i.e. the entrance electrode 15a and the exit electrode 15b provided with the proton conducting electrolyte membrane 15c sandwiched therebetween, enables hydrogen molecules in the measurement target gas present on the entrance electrode 15a side to ionize and permeate to the exit electrode 15b side, and to exist again as hydrogen molecules on the exit electrode 15b side. As for the proton conducting electrolyte membrane, "Nafion®" (made by Dupont), a type of fluorine series resins can be adopted, for example. And, while this phenomenon of hydrogen permeation is occurring, voltage applied between the electrodes is measured by a voltmeter 15e and current flowing through the electrodes is measured by an ammeter 15d, and based on these electrical behaviors, concentration of hydrogen in the measurement target gas is calculated by a hydrogen concentration calculation module 15f.

In the present specification, as a result of the afore-mentioned hydrogen permeation effect by the hydrogen concentration sensor 15, concentration of impurities (materials other than hydrogen are collectively referred to as "impurities") contained in the measurement target gas is increased on the entrance electrode 15a side. In addition, in the hydrogen concentration sensor 15, hydrogen that was permeated from the entrance electrode 15a to the exit electrode 15b side is be treated as appropriate, such as supplied to a system capable of using hydrogen, discharged out of the system, and the like, though not explicitly shown in FIG. 1. Modes for supplying permeated hydrogen to a fuel cell in the fuel cell system again will be disclosed in detail in embodiments discussed later.

Figure 2:
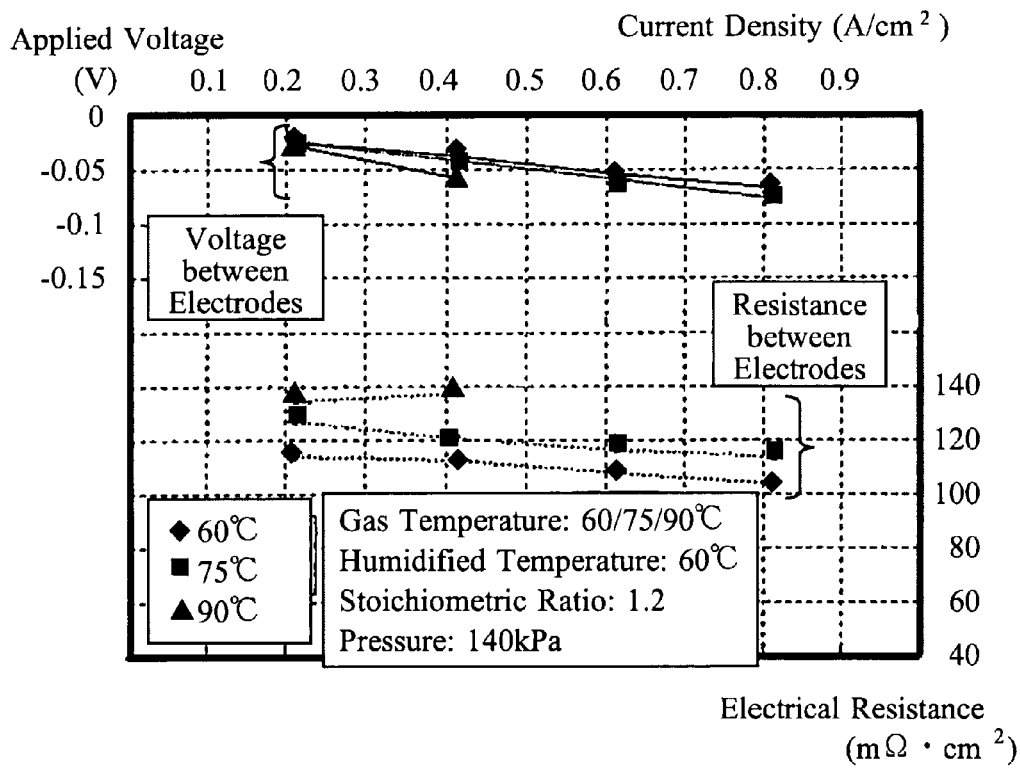
FIG. 2 is a diagram showing current-voltage characteristics of the hydrogen concentration sensor shown in FIG. 1.

Physical characteristics of the hydrogen concentration sensor 15 employing the proton conducting electrolyte membrane will now be described. FIG. 2 is a diagram showing current-voltage characteristics of the hydrogen concentration sensor 15, where the left vertical axis represents voltage applied between the electrodes, the right vertical axis represents electrical resistance between the electrode, and the horizontal axis represents density of current flowing between the electrodes. The graphs shown in the upper portion of FIG. 2 indicate correlations between the current density and the applied voltage; whereas the graphs shown in the lower portion of FIG. 2 indicate correlations between the current density and the electrical resistance. In each graph, measurement target gas targeted for measurement of hydrogen concentration has conditions of: a gas temperature of either 60° C., 75° C., or 90° C.; a humidified temperature of 60° C., a stoichiometric ratio of 1.2; and a pressure for supplying measurement target gas to the entrance electrode 15a of 140 kPa. In the graphs indicating the correlations described above, diamond shaped symbols are used as plots in case where measurement target gas has a temperature of 60° C., square shaped symbols are used as plots in case of 75° C., and triangle shaped symbols are used as plots in case of 90° C.

Figure 3:
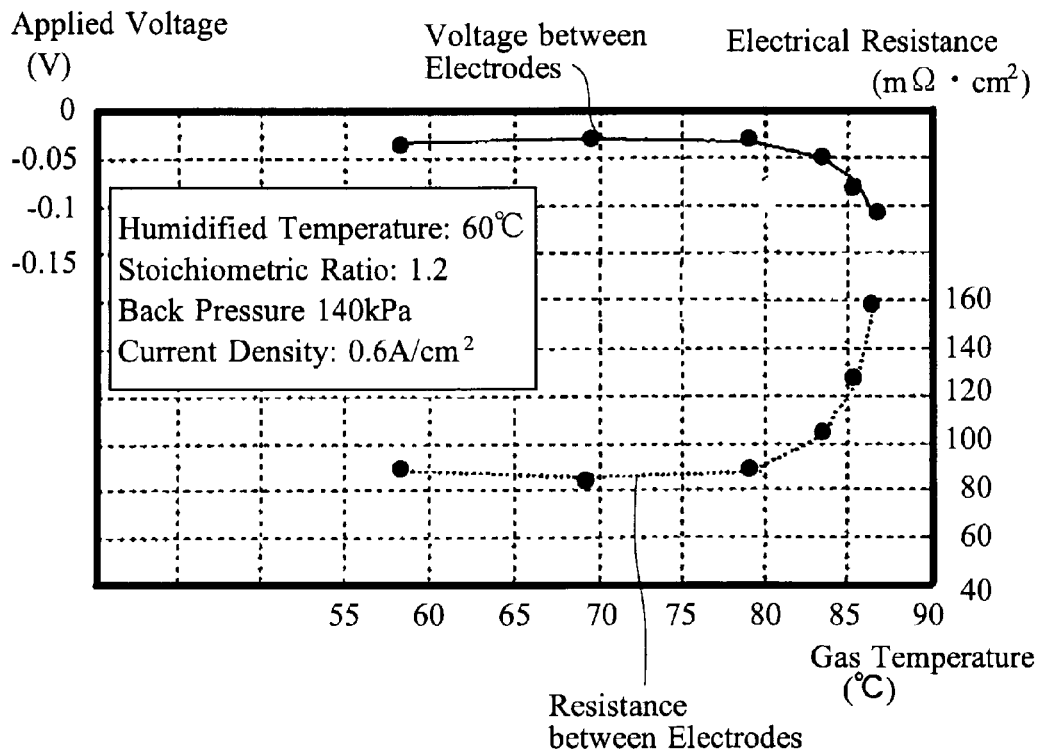
FIG. 3 is a diagram showing temperature characteristics of the hydrogen concentration sensor shown in FIG. 1.

Furthermore, FIG. 3 shows correlations between temperature of measurement target gas and applied voltage and electrical resistance between the electrodes, respectively, in case where measurement target gas of a temperature of 60° C. is supplied and current of a current density of 0.6 A/cm$^2$ flows between the electrodes. The left vertical axis represents voltage applied between the electrodes, the right vertical axis represents electrical resistance between the electrodes, and the horizontal axis represents temperature of measurement target gas. The graph shown in the upper portion of FIG. 3 indicates correlation between the temperature of measurement target gas and the applied voltage; whereas the graph shown in the lower portion of FIG. 3 indicates correlation between the temperature of measurement target gas and the electrical resistance.

As is clear from FIG. 2 and FIG. 3, the voltage applied between the electrodes in the hydrogen concentration sensor 15 highly depends on the electrical resistance between the electrodes. On the other hand, since the electrolyte membrane 15c constituting the hydrogen concentration sensor 15 has its wet state varied under the influence of temperature and humidity of the measurement target gas introduced into the entrance electrode 15a, the electrical resistance will be strongly affected by temperature and the like of the measurement target gas. Therefore, the applied voltage between the electrodes has variance depending on temperature and the like of the measurement target gas, so that if employing the variation of the applied voltage directly for measurement of hydrogen concentration, then result of measurement will have variance depending on temperature and the like of the measurement target gas, and thus, there will be no hope for high precision measurement. Especially, if there is possibility that temperature and the like of the measurement target gas have variation within a range having influence on wet state of the electrolyte membrane 15c, there will be no hope for high precision measurement.

Therefore, in the hydrogen concentration sensor 15, the variation of time rate of change of applied voltage between the entrance electrode 15a and the exit electrode 15b (hereinafter simply referred to as "time rate of change of applied voltage) is employed, rather than the variation of applied voltage between the electrodes itself, in measurement of hydrogen concentration of measurement target gas. If measurement target gas contains hydrogen targeted for measurement as well as impurities other than hydrogen, then hydrogen in the measurement target gas is permeated to the exit electrode 15b side as current flows between the electrodes, and results in increased proportion of impurities in the measurement target gas. And, along with the increased concentration of impurities in the measurement target gas, an effective surface area will be reduced to a state that shows a sharp increase in the applied voltage (hereinafter referred to as "difficult-to-conduct state"). If current flowing between the electrodes is controlled to be constant, then time rate of change of applied voltage will become larger as electrical state between the electrodes approaches this difficult-to-conduct state.

In light of the foregoing, a period of time ranging from a time at which the current was initially applied between the electrodes for measurement of hydrogen concentration in the hydrogen concentration sensor 15 to a time at which the difficult-to-conduct state is reached or a state just before the difficult-to-conduct state is reached (hereinafter simply referred to as "reaching time period") depends on a proportion of hydrogen to impurities in the measurement target gas at the time the gas was initially introduced into the entrance electrode 15a. That is, a predetermined correlation can be found between the reaching time period and the impurities concentration, in other words, the hydrogen concentration, such that the larger the proportion of impurities in the measurement target gas, the shorter the reaching time period. In addition, since the difficult-to-conduct state is a state where current density is locally large or a state of hydrogen deficiency, there is a sharp increase in voltage. In order to eliminate influence of temperature and the like of the measurement target gas as much as possible, it is preferable to make decision by using time rate of change of applied voltage, that is, a rate by which the applied voltage changes during measurement of hydrogen concentration. Since the time rate of change is calculated from change of the applied voltage over time, it may be possible to eliminate influence of temperature and the like of the measurement target gas on cell resistance. Therefore, in the hydrogen concentration sensor 15, time rate of change of applied voltage detected by the voltmeter 15e is calculated by the hydrogen concentration calculation module 15f, and further, hydrogen concentration of the measurement target gas is calculated based on a period of time that the time rate of change takes to reach a predetermined time rate of change i.e. a time rate of change that corresponds to the afore-mentioned difficult-to-conduct state.

Figure 4:
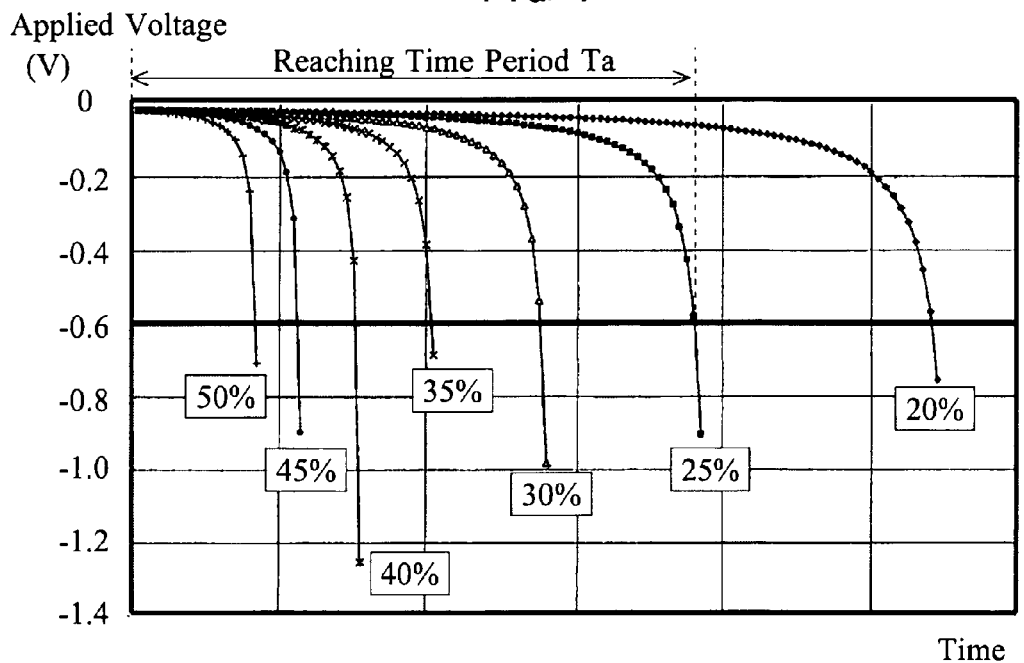
FIG. 4 is a diagram showing correlations between concentration of impurities contained in measurement target gas within an entrance electrode and change in applied voltage, of the hydrogen concentration sensor shown in FIG. 1.

Hereinafter, measurement of hydrogen concentration of measurement target gas will be described concretely with reference to FIG. 4 and FIG. 5. FIG. 4 shows temporal transitions of applied voltage, respectively corresponding to different impurities concentrations of measurement target gas introduced into the entrance electrode 15a (impurities concentrations at the time the measurement target gas was initially introduced), in case where the applied voltage is controlled such that constant current flows between the electrodes in the hydrogen concentration sensor 15. The tendency common to the temporal transitions of applied voltage is that the applied voltage shows a quite small change when it was initially applied, but shows a drastic change once a certain amount of time has passed. And, the larger the concentration of impurities in the measurement target gas within the entrance electrode 15a becomes as a result of hydrogen permeation due to continuous conduction, the shorter the time passes from the initial application of voltage to the drastic change of applied voltage.

Figure 5:
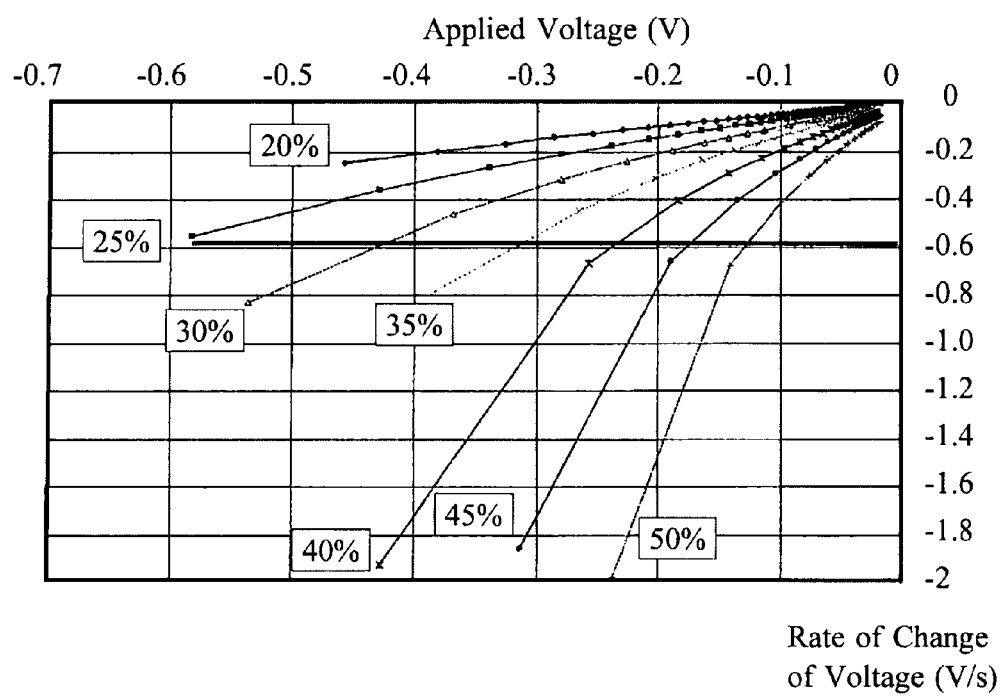
FIG. 5 is a diagram showing correlations between concentration of impurities contained in measurement target gas within an entrance electrode and rate of change of applied voltage, of the hydrogen concentration sensor shown in FIG. 1.

In addition, graphs indicating correlations between the applied voltage and the rate of change of voltage derived based on the characteristics of applied voltage shown in FIG. 4 are shown in FIG. 5. The rate of change of voltage is defined as a time rate of change of applied voltage, and is derived by differentiating the temporal transitions of applied voltage shown in FIG. 4 with respect to time. As seen, in cases where concentration of impurities in the measurement target gas is relatively low, such as 20% and 25%, the time rate of change of voltage can be kept relatively low even if the applied voltage is high to some extent; however, in case where concentration of impurities in the measurement target gas is relatively high, the time rate of change of voltage becomes very high even though the applied voltage is kept as low as in case of 20% or 25%, or even lower.

As is also clear from FIG. 4 and FIG. 5, the rate of change of voltage, which is also the time rate of change of applied voltage, has a strong correlation with a state where local current density is high and condensation has progressed, such as the difficult-to-conduct state. Therefore, with a predetermined rate of change of voltage as a reference set to $-0.6V/s$, an attention is focused on a time period Ta (reaching time period) that the rate of change of voltage requires to reach the predetermined rate of change of voltage since a time (start time) at which measurement target gas was introduced into the entrance electrode 15a and current was initially applied between the electrodes. In FIG. 4, the reaching time period Ta for a measurement target gas having an initial impurities concentration of 25% is illustrated. Since the reaching time period Ta varies depending on the initial impurities concentration as above, it is possible to measure concentration of hydrogen contained in the measurement target gas from this correlation between the reaching time period Ta and the impurities concentration. In addition, by using the rate of change of voltage, it is possible to avoid, to the full, the influence of increased cell resistance due to temperature and the like of the measurement target gas as described above.

Figure 6:
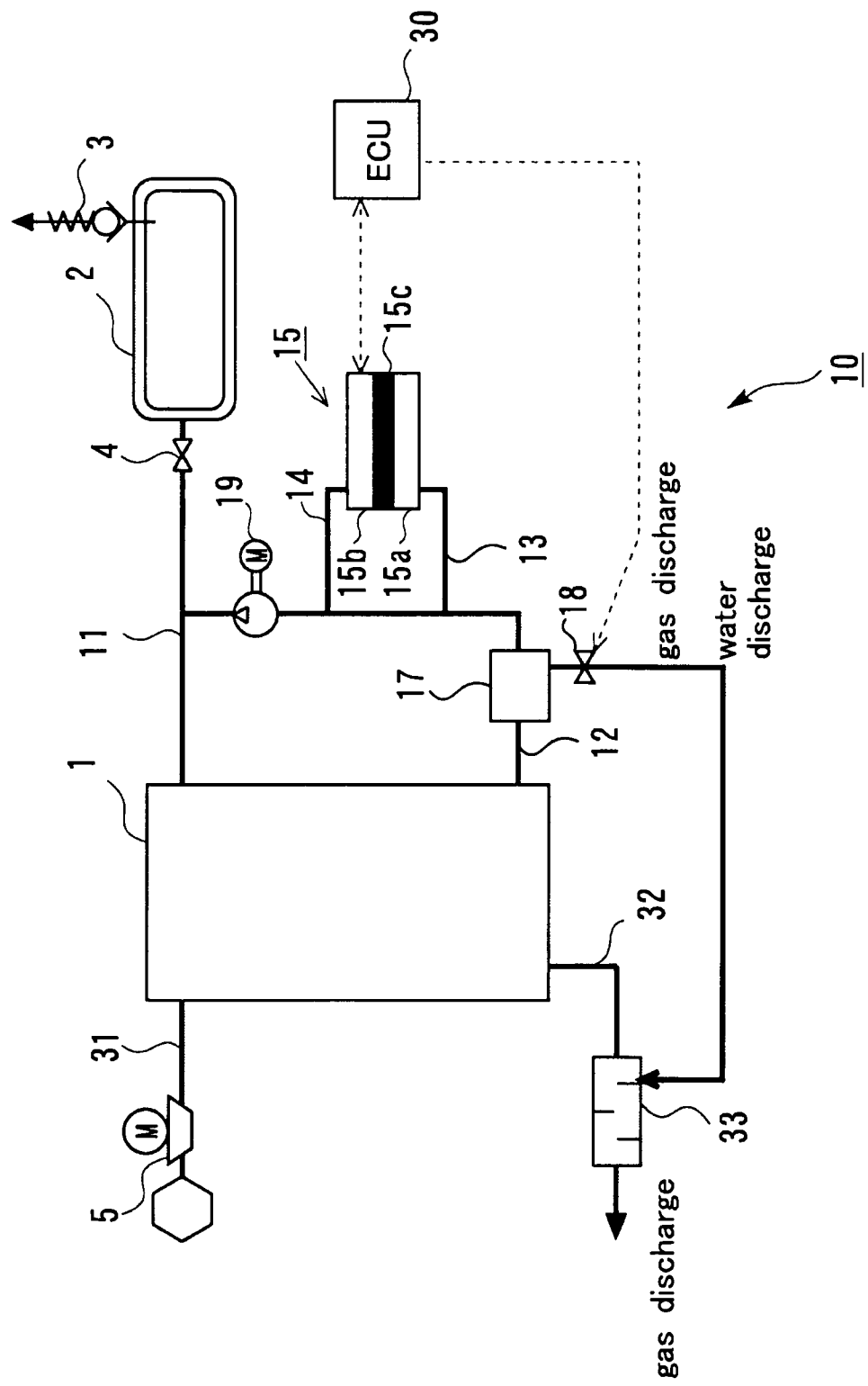
FIG. 6 is a first diagram showing general configuration of a fuel cell system including the hydrogen concentration sensor shown in FIG. 1.

A fuel cell system 10 is now illustrated in FIG. 6, as a system to which the hydrogen concentration sensor 15 described hereinabove is applied. This fuel cell system 10 can be adopted as a source of supply for supplying electric power to a drive motor that is a drive unit of a vehicle as a moving body, as a source of electric power supply in a moving body other than a vehicle such as a ship, robot, and the like, as a source of electric power supply for an object that does not move but requires supply of electric power.

This fuel cell system 10 has a proton exchange membrane fuel cell 1, and is provided with a high pressure hydrogen tank 2 that stores hydrogen gas as fuel and supplies the fuel to an anode electrode of the fuel cell 1 via a hydrogen supply channel 11. This high pressure hydrogen tank 2 is provided with an adjusting valve 3 for adjusting internal pressure thereof, and supply from the high pressure hydrogen tank 2 to the hydrogen supply channel 11 is conducted according to opening and closing of a supply valve 4. In addition, a compressor 5 that supplies air as oxidizing agent is connected to a cathode electrode of the fuel cell 1, and compressed air is supplied to the fuel cell 1 by the compressor 5 via an air supply channel 31. Then, the afore-mentioned supplied hydrogen and oxygen in this compressed air react electrochemically via an electrolyte membrane of the fuel cell 1, thereby generating electric power.

Here, in order to promote effective utilization of hydrogen gas that was supplied to the fuel cell 1 but was not used for electrochemical reaction for generation of electric power, the fuel cell system 10 is provided with a configuration for circulating anode offgas on the anode electrode side of the fuel cell 1. Concretely, anode offgas discharged from the anode electrode of the fuel cell 1 is delivered into a gas-liquid separator 17 via a circulation pathway 12, where moisture content contained in the anode offgas is removed. In addition, a pump 19 is provided on the circulation pathway 12 between the gas-liquid separator 17 and the hydrogen supply channel 11, and through pumping action of the pump 19, the anode offgas, from which moisture content was removed, is delivered to the hydrogen supply channel 11 again, thereby promoting reutilization of hydrogen gas contained in the anode offgas. Meanwhile, cathode offgas discharged from the fuel cell 1 is delivered into a diluter 33 though a discharge pathway 32, so does the anode offgas discharged via a discharge channel 16 connected to the electrochemical cell 150, so that concentration of hydrogen in the anode offgas is diluted by the cathode offgas and is released out of the system.

In a hydrogen circulation type of system such as the fuel cell system 1, hydrogen concentration of fuel gas to be delivered into the fuel cell 1 is decreased along with increased concentration of impurities in anode offgas flowing through the circulation pathway 12, therefore resulting in decrease in power generation efficiency. Accordingly, anode offgas in the circulation pathway 12 needs to be released out of the system on a regular basis. However, since unnecessarily repeating the release of anode offgas results in wasteful discard of hydrogen contained in the anode offgas, it is required to make timings to release the anode offgas adequate.

So, in the fuel cell system 10, the hydrogen concentration sensor 15 is placed to be parallel with a portion of the circulation pathway 12 between the gas-liquid separator 17 and the pump 19. In the hydrogen concentration sensor 15, the entrance electrode 15a is connected to the circulation pathway 12 via a communicative channel 13 and the exit electrode 15b is also connected to the circulation pathway 12 via a communicative channel 14, but the connecting location between the communicative channel 14 and the circulation pathway 12 lies more downstream, that is, closer to the hydrogen supply channel 11, than the connecting location between the communicative channel 13 and the circulation pathway 12 in a direction along the flow of anode offgas within the circulation pathway 12. Therefore, hydrogen that was permeated to the exit electrode 15b side in the hydrogen concentration sensor 15 flows through the circulation pathway 12 and is delivered into the hydrogen supply channel 11 again.

By having the fuel cell system 10 provided with the hydrogen concentration sensor 15 as just described, measurement of concentration of hydrogen in the circulation pathway 12 becomes possible. Especially the anode offgas as a measurement target gas flowing through the circulation pathway 12 has its temperature and humidity varied depending on operational condition of the fuel cell 1, so that application of the hydrogen concentration sensor 15 that is less susceptible to those factors may be quite useful.

Further, the fuel cell system 10 is provided with an electronic control unit (ECU) 30 that is responsible for operational control of the entire system. Although in FIG. 6, only control lines indicating electrical connections related to a part of the control for which the ECU 30 is responsible are shown by dotted lines, however, the ECU 30 may also perform controls on other configurations in the system as well. Note that the ECU 30 is connected to the hydrogen concentration sensor 15 and to the discharge valve 18 provided on the gas-liquid separator 17, and opening and closing of the discharge valve 18 is controlled based on hydrogen concentration measured by the hydrogen concentration sensor 15. When the discharge valve 18 is in a valve-closed state, moisture content separated by the gas-liquid separator 17 is temporarily stored in the system, while anode offgas in the circulation pathway 12 continues to be resupplied to the fuel cell 1. On the other hand, when the discharge valve 18 is in a valve-opened state, anode offgas in the circulation pathway 12 is released out of the system along with moisture content separated by the gas-liquid separator 17.

Figure 7:
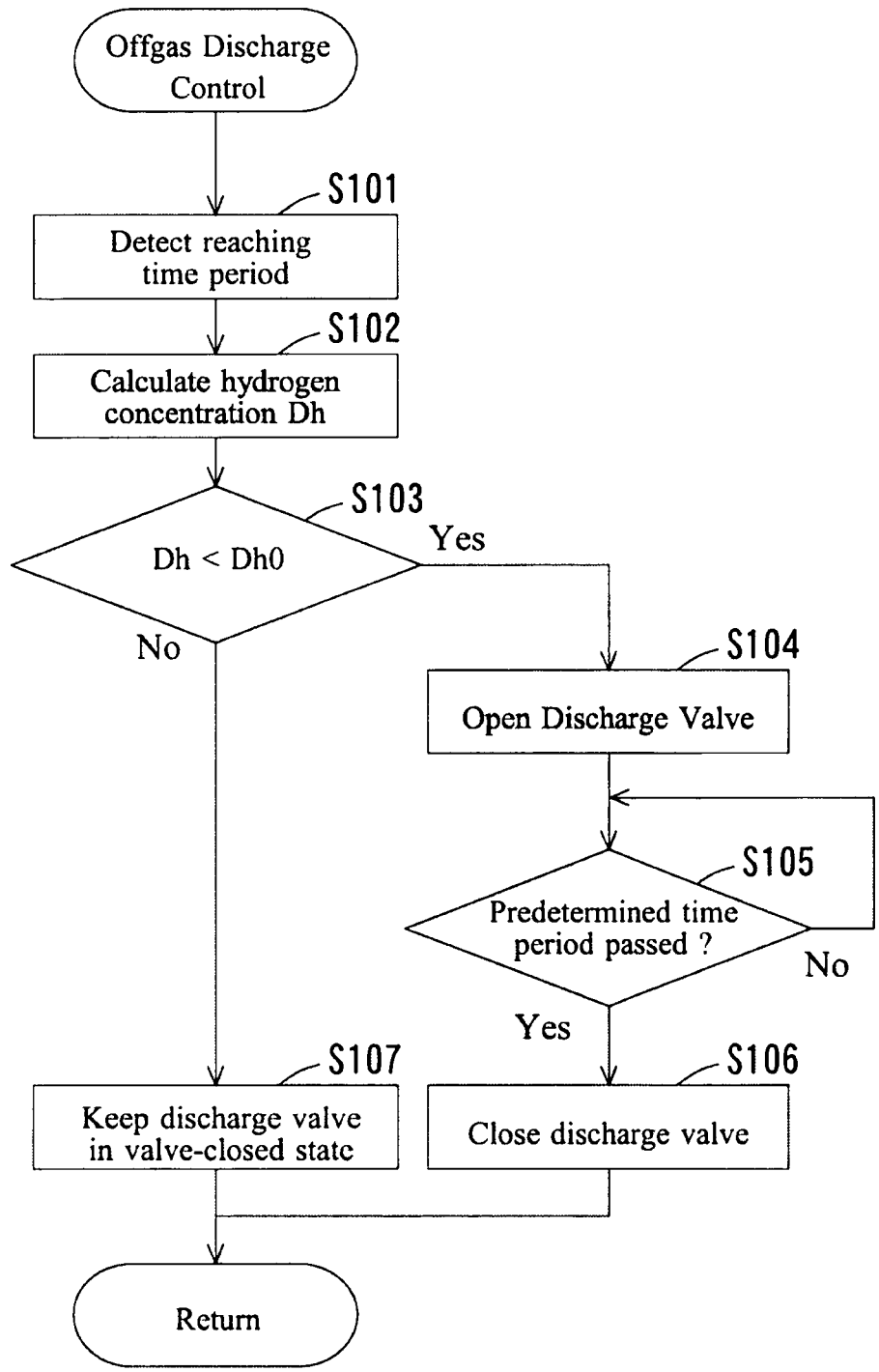
FIG. 7 is a control flow diagram for discharge of anode offgas, which is executed in the fuel cell system including the hydrogen concentration sensor shown in FIG. 1.

Here, a flowchart of timing control to be performed on discharge of anode offgas by the discharge valve 18, which is executed by the ECU 30 and employs result of measurement by the hydrogen concentration sensor 15 (hereinafter referred to as "offgas discharge control"), is shown in FIG. 7. This offgas discharge control is executed, by the ECU 30, at predetermined timings such as at regular intervals. At the beginning of the execution of control, the discharge valve 18 is in a valve-closed state.

Firstly, in S101, with anode offgas introduced into the entrance electrode 15a of the hydrogen concentration sensor 15, current is initially applied between the entrance electrode 15a and the exit electrode 15b for the purpose of hydrogen concentration measurement, and a reaching time period, which is a period of time that rate of change of voltage i.e. time rate of change of applied voltage takes to reach the afore-mentioned predetermined rate of change of voltage, is detected. Then, in S102, hydrogen concentration Dh, which is unambiguously determined from the detected reaching time period, is calculated as described above.

Next, in S103, a judgment is made on whether or not the hydrogen concentration Dh calculated in S102 is lower than a reference hydrogen concentration Dh0 for opening the discharge valve 18. This reference hydrogen concentration Dh0 is determined in advance based on the above-described balance between decrease in power generating efficiency in the fuel cell 1 and wasteful release of hydrogen. An affirmative judgment in S103 leads to S104; whereas a negative judgment in S104 leads to S107.

Next, if an affirmative judgment is made in S103 and the process proceeded to S104, then the discharge valve 18 is put to a valve-opened state, and anode offgas in the circulation pathway 12 is released out of the system. Then, the process proceeds to S105 thereafter, where a judgment is made on whether or not the predetermined time period was passed since the discharge valve 18 was opened. This predetermined time period is a period of time for which the discharge valve 18 stays in the valve-opened state. An affirmative judgment here leads to S106; whereas a negative judgment here leads to the judgment in S105 again. Next, in S106, the discharge valve 18 is returned to the valve-closed state. Once the processing in S106 ends, the offgas discharge control is executed again from S101.

Meanwhile, if a negative judgment is made in S103 and the process proceeded to S107, then the discharge valve 18 stays in the valve-closed state. That is, the anode offgas in the circulation pathway 12 is not released out of the system. Once the processing in S107 ends, the offgas discharge control is executed again from S101.

According to this offgas discharge control, times to discharge anode offgas by the discharge valve 18 can be made adequate, with no influence of operational condition of the fuel cell 1.

<Other Modes for Embodying the Fuel Cell System>

FIG. 8 shows general configuration of the fuel cell system 10 according to another embodiment. The same reference numbers are used for configurations same as those included in the fuel cell system 10 shown in FIG. 6, and are not described in detail. The fuel cell system 10 shown in FIG. 8 is a hydrogen circulation type of system, as with the fuel cell system shown in FIG. 6, however, is provided with an electrochemical cell 150 in place of the hydrogen concentration sensor 15.

The electrochemical cell 150 has an entrance electrode 150a and an exit electrode 150b provided with an electrolyte membrane 150c sandwiched therebetween, where the entrance electrode 150a is connected to a circulation pathway 12 via a communicative channel 130 and the exit electrode 150b is also connected to the circulation pathway 12 via a communicative channel 140, but the connecting location between the communicative channel 140 and the circulation pathway 12 lies more downstream, that is, closer to a hydrogen supply channel 11, than the connecting location between the communicative channel 130 and the circulation pathway in a direction along the flow of anode offgas within the circulation pathway 12.

And, the electrochemical cell 150 is a device that, by having current flowing between the two electrodes i.e. the entrance electrode 150a and the exit electrode 150b provided with the proton conducting electrolyte membrane 150c sandwiched therebetween, enables hydrogen molecules in anode offgas present on the entrance electrode 150a side to ionize and permeate to the exit electrode 150b side, and to exist again as hydrogen molecules on the exit electrode 150b side. That is, it is a device that, among anode offgas that was delivered into the entrance electrode 150a side, selectively causes hydrogen to permeate to the exit electrode 150b side, and as a result of this hydrogen permeation effect, impurities such as nitrogen contained in the anode offgas (hereinafter simply referred to as "impurities") can be condensed at the entrance electrode 150a side and concentration of hydrogen in the anode offgas circulated in the hydrogen supply channel 11 can be increased, so that improvement of hydrogen utilization efficiency can be promoted. In the present specification, the effect of impurities condensation occurring at the entrance electrode 150a side as a result of the afore-mentioned hydrogen permeation effect by the electrochemical cell 150 is sometimes referred to as the "effect of impurities condensation by the electrochemical cell 150" as well.

With the fuel cell system 10 provided with the electrochemical cell 150 as just described, it is possible to promote more efficient utilization of hydrogen. However, at the entrance electrode 150a side of the electrochemical cell 150, the effect of impurities condensation thereof results in reduction of hydrogen concentration at that place. Since there are some possibilities arise that exert various undesirable influences on the electrochemical cell 150 and the fuel cell 1 (For example, damage on the electrolyte membrane 150a, decrease in power generating efficiency in the fuel cell 1, and the like accompanied with increased applied voltage between the entrance electrode 150a and the exit electrode 150b), due to the reduction of hydrogen concentration, it is necessary to discharge anode offgas in the entrance electrode 150a out of the system at appropriate timings. Therefore, as a concrete configuration for discharging the anode offgas, the fuel cell system 10 is provided with a discharge channel 16 that is connected to most downstream side within the entrance electrode 150a (that is, at the time a part of anode offgas flowing through the circulation pathway 12 is delivered into the entrance electrode 150a via the communicative channel 130, suppose the location where the communicative channel 130 connects to the entrance electrode 150a is defined as most upstream side within the entrance electrode 150a, then most downstream side is located on the opposite side from the most upstream side) and a discharge valve 20 for controlling flow of gas flowing through the discharge channel 16. By having the discharge valve 20 opened, anode offgas within the entrance electrode 150a is allowed to be discharged out of the system. And, an ECU 30 is electrically connected to the electrochemical cell 150 and to the discharge valve 20, and eliminates undesirable influences on the electrochemical cell 15 and the like, such as deterioration of MEA due to hydrogen deficiency for example, by controlling opening and closing of the discharge valve 20 according to change of hydrogen concentration within the entrance electrode 150a, in other words, level of impurities condensation at the entrance electrode 150a.

In detail, since the electrochemical cell 150 has the entrance electrode 150a and the exit electrode 150b provided with the proton conducting electrolyte membrane sandwiched therebetween, as with the hydrogen concentration sensor 15 described above, it is possible to detect concentration of hydrogen contained in anode offgas introduced into the entrance electrode 150a by using these configurations, as with the hydrogen concentration sensor 15 (that is, as with the offgas discharge control shown in FIG. 7), from the aforementioned "reaching time period" that is detected based on time rate of change of voltage applied between the electrodes. Then, once the detected hydrogen concentration becomes lower than a reference hydrogen concentration for opening the discharge valve 20, then the mechanism of impurities condensation by the electrochemical cell can be operated, thereby putting hydrogen back into the hydrogen circulation system and reducing amount of hydrogen discharge, while maintaining condensation in the hydrogen circulation system in an adequate level.

What is claimed is:

1. A hydrogen concentration measurement device which measures concentration of hydrogen comprised in a measurement target gas, comprising:
   a hydrogen permeation module comprising an entrance electrode and an exit electrode provided with a proton conducting electrolyte membrane sandwiched therebetween, the hydrogen permeation module selectively permeating hydrogen comprised in the measurement target gas to the exit electrode by having the measurement target gas introduced into the entrance electrode, and also by having current flowing between the entrance electrode and the exit electrode;
   a current control module controlling current flowing between the entrance electrode and the exit electrode in the hydrogen permeation module; and
   a hydrogen concentration calculation module calculating concentration of hydrogen comprised in the measurement target gas based on, with the target gas introduced into the entrance electrode and with constant current flowing between the entrance electrode and the exit electrode by the current control module, a reaching time period ranging from a predetermined start time at which the current was initially applied to a time at which time rate of change of applied voltage between the entrance electrode and the exit electrode reaches a predetermined time rate of change which corresponds to a difficult-to-control state where, along with an increased concentration of impurities in the measurement target gas by having current flowing, a sharp increase in the applied voltage is shown,
   wherein the hydrogen concentration calculation module includes operable instructions to calculate the concentration of hydrogen comprised in the measurement target gas based on the reaching time period ranging from the predetermined start time at which the current was initially applied to the time at which time rate of change of applied voltage between the entrance electrode and the exit electrode reaches the predetermined time rate of change which corresponds to the difficult-to-control state.

2. A fuel cell system, comprising:

the device of claim 1, wherein the fuel cell system has hydrogen-comprising fuel gas supplied to an anode electrode side of a fuel cell for electrochemical reaction therein, wherein the fuel cell system has a circulation pathway such that a part or all of anode offgas from the fuel cell can be circulated to the anode electrode side of the fuel cell for the electrochemical reaction again, wherein the hydrogen concentration measurement device is disposed such that it is capable of measuring concentration of hydrogen in anode offgas in the circulation pathway by having the anode offgas flowing through the circulation pathway introduced into the entrance electrode; and wherein the anode offgas in the circulation pathway is discharged out of the system based on the hydrogen concentration measured by the hydrogen concentration measurement device.

3. The fuel cell system of claim 2, wherein:

hydrogen that was permeated to an exit electrode side by the hydrogen permeation module provided in the hydrogen concentration measurement device is supplied to the anode electrode side of the fuel cell again.

4. A fuel cell system, comprising:

the device of claim 1, wherein the fuel cell system has hydrogen-comprising fuel gas supplied to an anode electrode side of a fuel cell for electrochemical reaction therein, wherein the fuel cell system has a circulation pathway such that a part or all of anode offgas from the fuel cell can be circulated to the anode electrode side of the fuel cell for the electrochemical reaction again, wherein the hydrogen concentration measurement device is disposed such that it is capable of measuring concentration of hydrogen in anode offgas in the circulation pathway by having the anode offgas flowing through the circulation pathway introduced into the entrance electrode; and wherein the anode offgas in the circulation pathway is discharged out of the system based on the hydrogen concentration measured by the hydrogen concentration measurement device.

5. The fuel cell system of claim 4, wherein:

hydrogen that was permeated to an exit electrode side by the hydrogen permeation module provided in the hydrogen concentration measurement device is supplied to the anode electrode side of the fuel cell again.

* * * * *